United States Patent
Canham et al.

(10) Patent No.: US 6,929,950 B2
(45) Date of Patent: Aug. 16, 2005

(54) MICROPROJECTILE DELIVERY SYSTEM AND PARTICULATE PRODUCT

(75) Inventors: Leigh T Canham, Malvern (GB); Roger Aston, Malvern (GB)

(73) Assignee: pSiMedica Limited (GB)

( * ) Notice: Subject to any disclaimer, the term of this patent is extended or adjusted under 35 U.S.C. 154(b) by 85 days.

(21) Appl. No.: 10/240,931

(22) PCT Filed: Apr. 5, 2001

(86) PCT No.: PCT/GB01/01510

§ 371 (c)(1),
(2), (4) Date: Nov. 20, 2002

(87) PCT Pub. No.: WO01/76564

PCT Pub. Date: Oct. 18, 2001

(65) Prior Publication Data

US 2003/0134424 A1 Jul. 17, 2003

(30) Foreign Application Priority Data

Apr. 7, 2000 (GB) .............................. 0008494

(51) Int. Cl.⁷ .............................. C12N 15/87

(52) U.S. Cl. .................... 435/459; 435/470; 435/285.3; 423/324

(58) Field of Search ................................. 435/459, 470, 435/285.3; 423/324

(56) References Cited

U.S. PATENT DOCUMENTS

| 3,986,905 A | * | 10/1976 | Garavaglia .................. 438/562 |
| 5,354,564 A | | 10/1994 | Borish et al. |
| 5,527,386 A | | 6/1996 | Statz |
| 5,695,617 A | * | 12/1997 | Graiver et al. ......... 204/157.41 |
| 6,004,287 A | | 12/1999 | Loomis et al. |

FOREIGN PATENT DOCUMENTS

| EP | A-0727678 | 8/1996 |
| EP | 0 727 678 B1 | 3/2003 |
| JP | 05 330817 A | 12/1993 |
| JP | 06 072705 A | 3/1994 |
| WO | WO 91/07487 | 5/1991 |
| WO | WO 99/29498 | 6/1999 |
| WO | WO 99/53898 | 10/1999 |
| WO | WO 00 05339 | 2/2000 |

OTHER PUBLICATIONS

Wu et al, "Submicron silicon powder production in an aerosol reactor", Applied Physics Letters, vol. 49, No. 2, Jul. 14, 1986.

* cited by examiner

Primary Examiner—James Ketter
(74) Attorney, Agent, or Firm—Nixon & Vanderhye P.C.

(57) ABSTRACT

The invention relates to a particulate product comprising at least one microprojectile; characterized in that the or at least one of the microprojectiles comprises silicon. The invention also relates to devices and components used in the microprojectile implantation of the particulate product to a target of cells or target tissue.

10 Claims, 11 Drawing Sheets

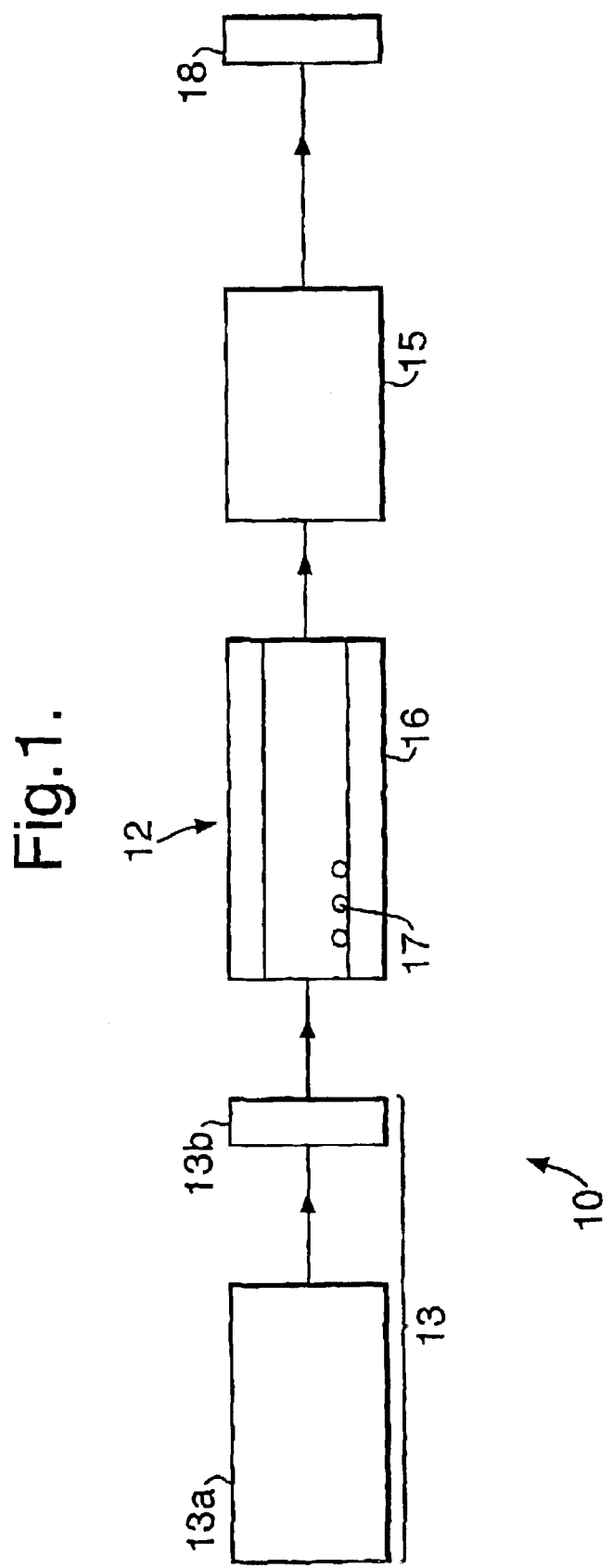

Fig.3.
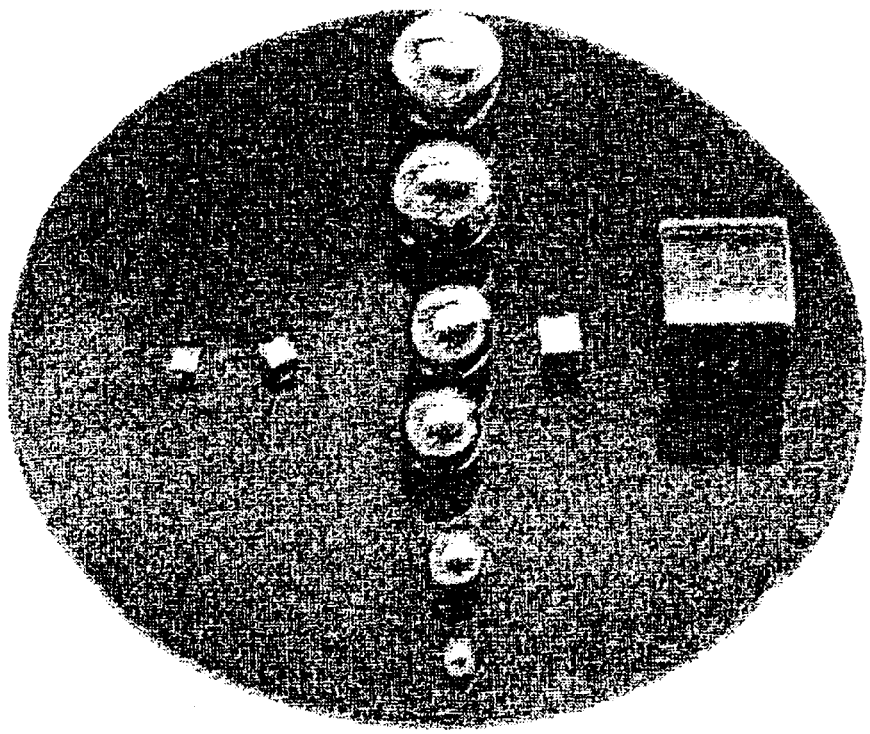
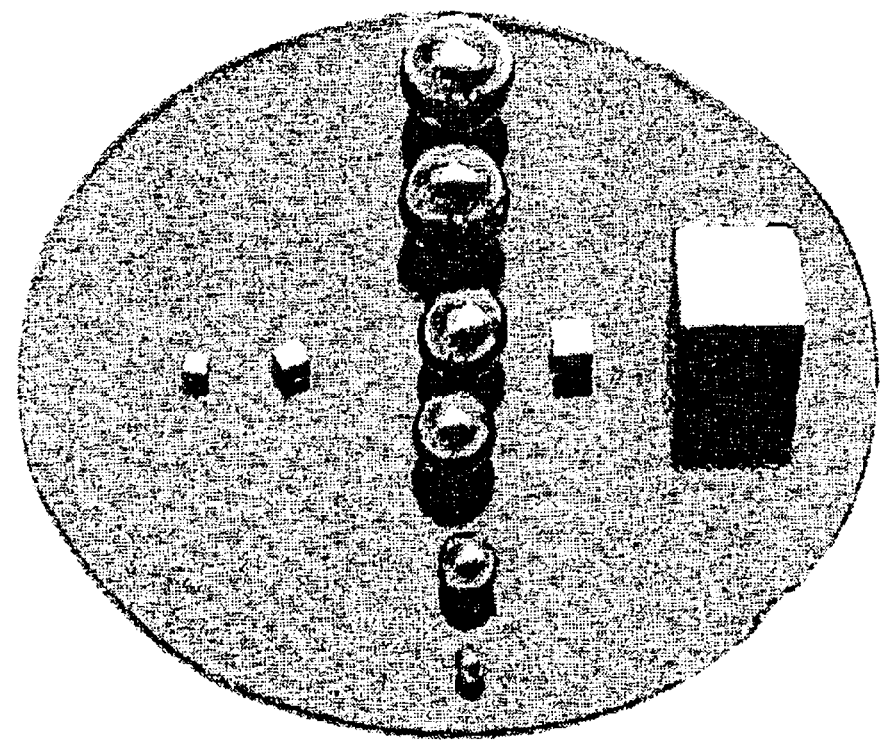

Fig.10.
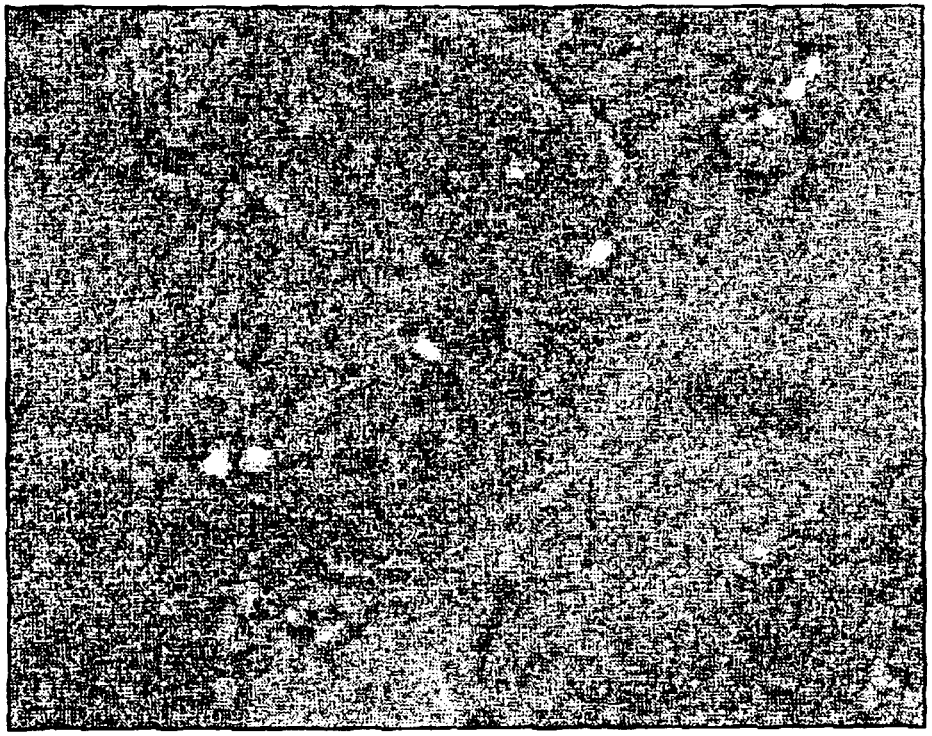
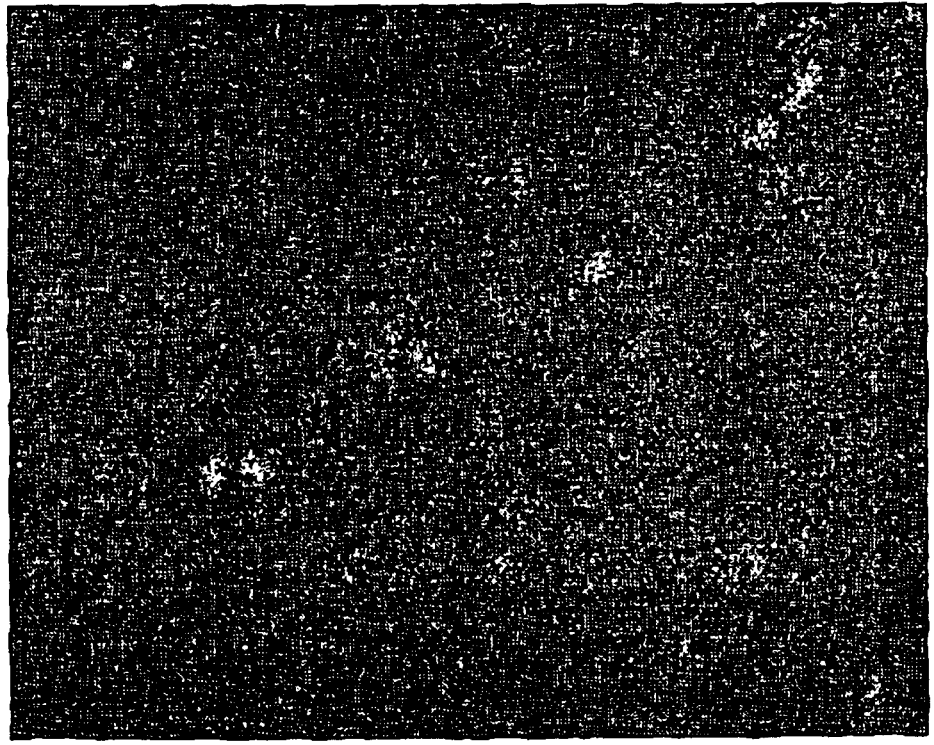

MICROPROJECTILE DELIVERY SYSTEM AND PARTICULATE PRODUCT

BACKGROUND OF THE INVENTION

The present invention relates to new products that may be implanted into cells or a target tissue. The invention also relates to components and devices that may be used in the delivery of said products to cells and tissues. In a further aspect, the invention relates to methods of fabricating said products, components, and devices. In a yet further aspect the invention relates to a new particulate product.

It is known that gold particles coated with DNA may be used to transfer DNA into cells. This is achieved by accelerating the particles towards a target of cells. The particles then pass through the cell walls and/or membranes carrying the DNA into the cell. Compressed gas such as helium is commonly used to bring about this acceleration.

A similar technique has also been developed to inject particles through the skin of a patient. Again the particles are accelerated by compressed gas and pass through the skin into the body of the patient. The particles can be used to inject drugs, DNA, or vaccines to the blood stream or tissues of humans or animals.

The implantation of particles into tissue or cells in this way is known as microprojectile implantation, and involves acceleration of a particle to a velocity that allows it to penetrate a cell wall and/or membrane or to penetrate tissue. Microprojectile implantation differs from other forms of implantation since it is the momentum of the particle that causes the breach in the cell wall or tissue, as opposed to an implement such as a needle or surgeon's knife. A further factor that affects implantation depth and degree of tissue damage is the shape of the microprojectile particle.

Microprojectile implantation has several advantages over other forms of implantation. The technique makes it easier for human patients to self administer an active substance, eliminating the use of needles. The active substance can be used in dry form, potentially increasing stability of many active substances. The procedure is significantly less painful than needle delivery and is hence particularly favoured for paediatric use. Finally since the active substance can be delivered in particulate form the release of the substance may, in certain circumstances, be better controlled.

A microprojectile is a particle having a composition, size, shape, and mass such that it is suitable for microprojectile implanation into a target tissue or cell, or into the blood stream of a patient. If the microprojectile is being administered to tissue (eg skin), the velocity and momentum must be set to achieve the correct level of penetration in order to achieve the desired physiological effect. Microprojectiles are typically used in association with an active substance, such as a drug or biological material. The properties that make the particle suitable for microprojectile implantation will depend upon the active substance to be delivered to the target, upon the technique used to deliver the particles, and upon the target tissue or cell. For example if a microprojectile is to be introduced into a cell, then its constitution and velocity must allow it to penetrate the cell wall and/or cell membranes without destroying the cell. Typically the particle must be approximately one tenth the size of the cell to be implanted. If, on the other hand, it is for extracellular drug delivery, its size is significantly larger, and often in the 10 to 100 micron range.

The active substance may be coated onto the microprojectile, for example DNA may be precipitated onto the surface of gold particles. In the case of a drug to be implanted in a patient, the microprojectile may simply consist of an excipient combined with the drug. A relatively low density material such as ice may be used as a carrier material for the active substance: the substance may be dissolved or otherwise combined with water; the solution/suspension is then nebulised and the resulting droplets frozen. The frozen droplets can then be implanted into the cells where the ice melts releasing the substance.

A number of devices may be used to deliver microprojectiles to the target cells or tissue. Such devices (delivery devices) typically comprise a gas source and a component (a carrier component) for retaining the microprojectiles prior to delivery. The gas source is often a small pressurised helium cylinder and can be activated by puncturing the cylinder to release a flow of helium. The device, often termed a gene gun if the material to be delivered is genetic, may be arranged so that the flow of helium causes the microprojectiles to be accelerated towards the target. For example the carrier component may comprise a disc upon which the microprojectiles are adhered, the flow of gas causing them to be dislodged from the disc. The carrier component and gas source are usually designed to facilitate their replacement so that the microprojectile delivery device may be used many times.

It is known that products may be implanted in human or animal patients by techniques other than microprojectile implantation. For example an implant may be introduced surgically or by injection though a needle. Both these techniques are referred to in PCT/GB99/01185, which describes the use of porous and polycrystalline silicon implants. There are several types of porous and polycrystalline silicon including: biocompatible silicon, bioactive silicon, and resorbable silicon. The fabrication and properties of these three types of silicon are referred to in PCT/GB96/01863.

There are a number of problems associated with existing microprojectiles. Many microprojectiles currently used are only able to carry a small amount of active substance in relation to their size. Prior art microprojectiles are typically solid, so that the active substance is confined to the surface of the microprojectile. The surface location of the active substance means that it is exposed to forces during passage of the microprojectile into the target, and is therefore vulnerable to damage. Where the active substance comprises large organic molecules such as DNA, then passage of the microprojectiles through the skin of a patient may cause the DNA molecules to fragment. The immune response of a patient may also cause deactivation of the substance as a result of its surface location.

Prior art microprojectiles, which have sufficient mechanical strength to withstand the forces of implantation, are typically fabricated from materials that are insoluble in biological environments. This can hinder the release of the active substance into the cell or tissue. For example DNA present on the surface of gold particles is immobilised by the gold, hindering transfection of the DNA. This immobilisation means that the DNA may be degraded before it can be intercalated into the nucleus of the implanted cell. Though in some cases it may be advantageous for the DNA to remain on the gold in an active form. Another material commonly used in the fabrication of microprojectiles is tungsten. Tungsten is inexpensive relative to gold, but it suffers from several disadvantages. It is difficult to fabricate tungsten microprojectiles having as uniform size distribution. Tungsten is also potentially toxic; and finally is also known to catalytically degrade DNA bound to its surface.

The factors that affect whether a material is suitable for use in microprojectile implantation are therefore complex. Properties such as density, toxicity, mechanical strength, internal structure, surface properties, and solubility in a variety of environments, may all affect the performance of the material.

SUMMARY OF THE INVENTION

It is an object of the present invention to provide products that better satisfy the requirements associated with microprojectile delivery of an active substance to cells or tissue. It is a further object of the present invention to provide components and devices that also better satisfy the requirements associated with microprojectile delivery of an active substance to a cells or tissue. It is a yet further object of the invention to provide methods of fabricating said products, components, and devices.

According to a first aspect the invention provides a particulate product comprising at least one silicon particle.

The or each silicon particle comprises silicon.

The or at least one of the silicon particles may comprise one or more of: porous silicon, polycrystalline silicon, resorbable silicon, bioactive silicon, bulk crystalline silicon, biocompatible silicon, and amorphous silicon.

If the particulate product comprises more than one silicon particle, then the silicon particles from which the product is formed need not all comprise the same type of silicon. For example some of the particles may comprise porous silicon and others may comprise bulk crystalline silicon.

Advantageously the or at least one of the silcon particles is a microprojectile.

For the avoidance of doubt a microprojectile is a particle having a composition, size, shape, and mass such that it is suitable for microprojectile implanation into a target tissue or cell, or into the blood stream of a patient.

Preferably the microprojectile has a composition, size, shape and mass such that it is suitable for microprojectile implantation into a human or animal.

Advantageously the or at least one of the microprojectiles has an elongated shape. More advantageously the or at least one of the microprojectiles has a pointed tip. Yet more advantageously the or at least one of the microprojectiles comprises a microneedle.

The or at least one of the microprojectiles may comprise a microbarb and/or a microdart.

Preferably the or at least one of the microprojectiles comprises porous and/or polycrystalline silicon.

Advantageously the or at least one of the microprojectiles has a composition, size, shape, and mass such that they are suitable for use in one or more of the devices disclosed in U.S. Pat. Nos. 5,204,253; 5,219,746; 5,506,125; 5,584,807; 5,865,796; 5,877,023; 5,919,159; 6,004,287; and 6,013,050, which are hereby incorporated by reference.

The particulate product may comprise a multiplicity of microprojectiles, the microprojectiles forming a powder. The powder may have a substantially uniform particle size distribution.

A number of advantages are associated with the use of silicon, particularly porous and/or polycrystalline silicon, in the fabrication of microprojectiles.

Porous and polycrystalline materials, if they have suitable nanostructure, exhibit visible-near infrared fluorescence. The fluorescence of the porous and polycrystalline silicon may be of value in monitoring drug concentrations in the blood of a patient, as well as the presence and quality of the implanted microprojectile. This is of particular value silicon devices comprising resorbable silicon. Where the blood of a patient contains microprojectiles with which a drug has been combined, analysis of a blood sample containing the microprojectiles could yield information about the drug and microprojectile concentration. The fluorescence allows the microprojectiles to be identified and their numbers to be determined with relative ease.

The fabrication of microprojectiles from silicon allows the use of silicon processing technologies. These silicon processing techniques, in turn, open the way for exquisite control over microprojectile shape and size, coupled with high yields and high purity products. Better control over not only the size, but also the shape of an assembly of microprojectiles will result in better control of the depth of penetration of tissue or their incorporation within target cells. The use of porous silicon microprojectiles is also advantageaous since the presence of pores allows a greater dose, and flexibility of loading of, active substance to be delivered for a given microprojectile size.

The or at least one of the microprojectiles may further comprise a high density material having a density greater than that of bulk crystalline silicon. The high density material may comprise one or more of: gold, tungsten, platinum, iron, nickel, molybdenum, silver, palladium, erbium, iridium, rhenium, and cobalt. The microprojectile may comprise a silicide. The silicon, from which the microprojectile is formed, may be located at the surface of the high density material.

The use of a material having a density greater than that of bulk crystalline silicon may be of particular value in intercellular microprojectile delivery.

The or at least one of the microprojectiles may comprise bulk crystalline silicon.

The or at least one of the microprojectiles may have a mass in the range 0.001 ng to 5 ng. The or at least one of the microprojectiles may have a mass in the range 1 ng to 1 $\mu$g. The or at least one of the microprojectiles may have a mass in the range 1 ng to 5 ng.

The 1 ng to 1 $\mu$g mass range may be of particular value in the delivery vaccines to cells. The 0.001 ng to 1 ng mass range may be of particular value in drug delivery to target tissues.

Advantageously the or at least one of the silicon particles further comprises an active substance.

The active substance may comprise one or more of: a pharmaceutical material, a biological material, a genetic material, a radioactive material, an antibacterial agent, and luminescent agent.

The active substance may comprise one or more of: insulin, lidocaine, anaesthetic, alprostadil, calcitonin, DNA, RNA, peptide, cytokine, hormone, antibody, cytotoxic agent, adjuvant, steroid, and protein.

The active substance may comprise one or more of: GnRH, Goserilin, Leuprordin Acetate, Triptordin, Buserelin, a GnRH agonist, a GnRH superagonist, a GnRH antagonist, a GnRH homologue, a GnRH analogue, and a GnRH mimic.

For the purposes of this specification the term active substance means any substance to be transferred into a target cell or tissue or into a patient.

Advantageously the active substance comprises DNA or RNA.

The active substance may be disposed, at least partly, in the interior of the or at least one of the silicon particles. The or at least one of the silicon particles may comprise porous silicon and the active substance may be disposed, at least partly, in the pores of the porous silicon. Alternatively the or at least one of the silicon particles may comprise a cavity that is bounded, at least partly, by the silicon. The active substance may be disposed in said cavity.

If the silicon particle comprises an active substance that is disposed in a cavity at least partly bounded by the silicon, or that is disposed in the pores of porous silicon; then the active substance will be protected from the effect of implantation into the cells or tissue. For example if the active substance comprises DNA, then the DNA will be protected from shearing forces as it passes through the tissue or cell walls.

Preferably the or at least one of the microprojectiles comprises resorbable silicon.

Advantageously the silicon comprises derivatised silicon. More advantageously the silicon comprises derivatised porous and/or polycrystalline silicon. Yet more advantageously the derivatised silicon comprises one or both of: Si—C bonding, and Si—O—C bonding.

As is well known in the art, the term "derivatised porous and/or polycrystalline silicon" means porous and/or polycrystalline silicon that has been derivatised predominantly or exclusively at the surface of the silicon.

By selecting appropriate derivatisation, the surface functionality of the microprojectile may be tailored to meet the requirements of the active substance.

The use of resorbable silicon is of value since resorbable silicon is known to dissolve or corrode in biological environments. The use of an active substance associated with resorbable silicon therefore opens the way for the controlled release of the active substance as a result of the corrosion/dissolution of the resorbable silicon. If the resorbable silicon is porous then the active substance may be disposed in the pores of the porous silicon; corrosion of the silicon may then release the substance from the pores. If the microprojectile comprises a cavity, in which an active substance is disposed and which is bounded by resorbable silicon, then corrosion of the silicon may also result in release of the substance.

The use of resorbable silicon microprojectiles potentially allows the delivery of large quantities of an active substance, relative to prior art microprojectiles. For example gold microprojectiles are only able to deliver active substances from the surface of the microprojectile. The use of resorbable silicon allows delivery of the whole active substance payload, throughout the volume of the microprojectile.

Advantageously the or at least one of the silicon particles comprises porous silicon having a porosity between 1% and 90%. More advantageously the porous silicon has a porosity between 10% and 80%.

Preferably the or at least one of the silicon particles may have a size in the range 100 nm to 500 $\mu$m. More preferably the or at least one of the silicon particles has a size in the range 100 nm to 250 $\mu$m.

The or at least one of the silicon particles may have a size in the range 10 $\mu$m to 100 $\mu$m. The or at least one of the silicon particles may have a size in the range 10 $\mu$m to 70 $\mu$m. The or at least one of the silicon particles may have a size in the range 1 $\mu$m to 15 $\mu$m.

The size range 10 $\mu$m to 100 $\mu$m may be of particular value for extracellular drug microprojectile delivery. The size range 1 $\mu$m to 15 $\mu$m may be of particular value for intracellular microprojectile delivery.

Advantageously the particulate product comprises at least five substantially single sized silicon particles, each single sized silicon particle having a volume that is substantially identical to the volume of the other single sized particles. More advantageously the particulate product comprises at least ten substantially single sized silicon particles, each single sized silicon particle having a volume that is substantially identical to the volume of the other single sized particles. Yet more advantageously the particulate product comprises at least twenty substantially single sized silicon particles, each single sized silicon particle having a volume that is substantially identical to the volume of the other single sized particles.

Preferably the particulate product comprises a multiplicity of single shaped silicon particles, each single shaped silicon particle having the substantially same shape as the other single shaped silicon particles. More advantageously each single shaped silicon particle has the substantially the same volume as the other single shaped silicon particles. Yet more advantageously each single shaped silicon particle is substantially symmetric.

The total mass of the single shaped silicon particles, from which the particulate product is at least partly formed, may be greater than 10% of the total mass of the particulate product. The total mass of the single shaped silicon particles, from which the particulate product is at least partly formed, may be greater than 50% of the total mass of the particulate product.

The particulate product may comprise a multiplicity of silicon particles and at least some of said silicon particles may be monodispersed.

Advantageously the or at least one of the silicon particles is substantially symmetric. More advantageously the particualte product comprises a multiplicity of substantially symmetric silicon particles, each substantially symmetric silicon particle being substantially symmetric.

The or at least one of the silicon particles may be substantially cubic. The or at least one of the silicon particles may be substantially spherical.

For the purposes of this specification the term "symmetric", when used to describe an object, means that the object comprises at least one plane of symmetry and/or at least one axis of symmetry.

According to a second aspect the invention provides a carrier component, for use in microprojectile implantation, comprising a carrier body and at least one microprojectile, the carrier body having a shape and being arranged such that the carrier body retains the or at least one of the microprojectiles, characterised in that the or at least one of the microprojectiles comprises silicon.

Carrier components (and hence the carrier body) are usually used in microprojectile delivery devices. They are designed to facilitate removal and replacement of the component in the device.

The carrier body may have a shape and be arranged such that it forms a cartridge, the or at least one of the microprojectiles being disposed within the cartridge. The carrier body may comprise a carrier wall, the or at least one of the microprojectiles being adhered to, or integral with, said carrier wall.

Advantageously the microprojectile comprises porous and/or polycrystalline silicon.

According to a third aspect, the invention provides a delivery device comprising at least one microprojectile and an activatable gas source; the gas source being arranged such that, when activated, it causes gas to impart kinetic energy to the or at least one of the microprojectiles; characterised in that the or at least one of the microprojectiles comprises silicon.

The gas may impart kinetic energy to the microprojectiles by direct impact of the gas with the microprojectiles. Alternatively the microprojectiles may be adhered to one side of a disc; in which case the microprojectiles may be accelerated by impact of the gas with the disc surface opposite to that on which the particles are adhered.

When the device is arranged appropriately, impact of the gas with the microprojectiles (or a body to which the microprojectiles are adhered) causes them to accelerate towards the target cells or tissue.

The gas source may comprise a reservoir, containing gas held under pressure and having a reservoir wall that encloses the gas. The gas source may be activated by rupturing the wall, thereby causing the gas to flow from the interior to the exterior of the reservoir.

The microprojectile delivery device need not comprise a reservoir of gas. The gas source may, for example, simply comprise a gas conduit attached by a tube to a cylinder; the cylinder being separate from the device. In this case the gas source may be activated by opening a valve between the tubing and the conduit.

The gas source may comprise an explosive, such as gunpowder; the gas source being activated by ignition of the explosive.

The microprojectile delivery device may further comprise a carrier body the carrier body having a shape and being arranged such that the carrier body retains the or at least one of the microprojectiles.

Preferably the microprojectile comprises porous and/or polycrystalline silicon.

According to a fourth aspect, the invention provides a method of fabricating a particulate product comprising the steps: (a) taking a sample of silicon and (b) forming at least one silicon product particle from the sample of silicon.

The silicon sample comprises silicon and the or each of the silicon product particles comprises silicon.

The sample of silicon may comprise one or more of: porous silicon, polycrystalline silicon, resorbable silicon, bioactive silicon, bulk crystalline silicon, biocompatible silicon, and amorphous silicon.

The or at least one of the silicon product particles may comprise one or more of: porous silicon, polycrystalline silicon, resorbable silicon, bioactive silicon, bulk crystalline silicon, biocompatible silicon, and amorphous silicon.

Preferably step (b) is performed in such a manner that at least one of the silicon product particles is a microprojectile.

Advantageously step (b) is performed in such a manner that at least one of the silicon product particles is symmetric. Yet more advantageously step (b) is performed in such a manner that a multiplicity of symmetric silicon product particles.

Step (b) may be performed in such a manner that at least five single sized silicon product particles are formed, each single sized silicon particle having a volume that is substantially identical to the other single sized product silicon particles.

Step (b) may be performed in such a manner that a multiplicity of single shaped product silicon particles are formed, each single shaped silicon product particle having a shape that is substantially identical to the other single shaped silicon product particles.

The method of fabricating a particulate product may comprise the further step (c) of porosifying said sample of silicon and/or porosifying the or at least one of the silicon product particles formed from the sample of silicon.

If the porosification step (c) involves the porosification of the or at least one of the silicon product particles, then the porosification may be performed in such a manner that it does not substantially alter the size and/or shape of the silicon product particle.

The method of fabricating a particulate product may comprise the further step (d), performed prior to steps (b) and (c), of forming the sample of silicon by depositing a layer of polycrystalline silicon on a substrate.

The particle forming step (b) may be performed prior to or after step (c). In other words the silicon product particles may be formed from porous or non-porous silicon.

Advantageously the particle forming step (b) is performed after step (c) and comprises the step of mechanically crushing said porous silicon.

Preferably the sample of silicon comprises a silicon wafer and step (b) comprises the step of etching the wafer. The step of etching the wafer may performed in such a manner that a multiplicity of monodispersed silicon product particles are formed; said monodispersed silicon product particles having a uniform size and/or shape.

The step (b) may comprise the step of photolithographically etching the wafer.

Advantageously step (b) is performed in such a manner that the or at least one of the silicon product particles has a size in the range 1 nm to 500 $\mu$m. More advantageously the or at least one of the silicon product particles has a size in the range 1 nm to 250 $\mu$m.

Step (b) may be performed in such a manner that the or at least one of the silicon product particles has a size in the range 10 $\mu$m to 100 $\mu$m. Step (b) may be performed in such a manner that the or at least one of the silicon product particles has a size in the range 10 $\mu$m to 70 $\mu$m. Step (b) may be performed in such a manner that the or at least one of the silicon product particles has a size in the range 1 $\mu$m to 15 $\mu$m.

Step (c) may comprise the step of anodising said sample of silicon. Step (c) may comprise the step of electrochemical etching said sample of silicon.

Preferably the step (c) comprises the step of applying a stain etch solution to the or at least one of the silicon product particles and/or applying a stain etch solution to the sample of silicon. More preferably the stain etch solution comprises hydrofluoric acid and an oxidising agent. Yet more preferably the stain etch solution comprises hydrofluoric acid and one or more of: nitric acid, sodium nitrite, and chromium trioxide. Even more preferably the stain etch solution comprises hydrofluoric acid and nitric acid; wherein the concentration of hydrofluoric acid, in the stain etch solution, is in the range 10 to 30 mol per litre and the concentration of nitric acid, in the stain etch solution, is in the range 0.0016 to 0.32 mol per litre.

Advantageously the process for fabricating a particulate product comprises the step of bombarding the or at least one of the silicon product particles, and/or bombarding the sample of silicon, with one or more of: ions, neutrons, and electrons; and further comprises the step of porosifying the silicon contained in the or at least one of the silicon product particles, and/or contained in the sample of silicon, that has been so bombarded.

Preferably the step of porosifying the silicon contained in the or at least one of the silicon product particles, and/or the silicon contained in the sample of silicon, comprises the step of light assisted porosification.

Preferably step (d) comprises the step of reacting a silicon containing gas in the region of the substrate. More preferably step (d) comprises the step of pyrolysing a silane and/or halogen substituted silane in the region of the substrate. Yet more preferably step (d) comprises the step of pyrolising $SiH_4$ in the region of the substrate.

Preferably step (b) comprises the steps: (i) mechanically processing the sample of silicon in such a manner that at least one intermediate silicon particle, is/are formed, the or each intermediate particle having a volume that is less than that of the sample of silicon from which it was formed; and (ii) applying a size reduction etch to the or at least one of the intermediate silicon particles, the etch being performed in such a manner that it reduces the size of the or at least one of the intermediate silicon particles.

The size reduction etch (ii) may be performed in such a manner that it does not substantially alter the shape of the or at least one of the intermediate silicon particles.

Preferably the step (i) of mechanically processing the sample of silicon comprises the step of dicing and/or sawing and/or milling and/or crushing and/or polishing and/or grinding the sample of silicon.

Advantageously the step (ii) of mechanically processing the sample of silicon is performed in such a manner that a multiplicity of monodispersed intermediate silicon particles are formed, each monodispersed intermediate silicon particle having substantially the same size and/or shape.

The size reduction etch (ii) may comprise a wet etch. The size reduction etch (ii) may comprise an isotropic etch. The size reduction etch (ii) may comprise a planar etch.

Advantageously the step (ii) of applying a size reduction etch comprises the step of applying a size reduction etch solution to the or at least one of the intermediate silicon particles, the etch solution comprising hydrofluoric acid and nitric acid. More advantageously the size reduction etch (ii) solution comprises hydrofluoric acid, nitric acid, and ethanoic acid, the concentration of the hydrofluoric acid, in the size reduction etch solution, being in the range 1.1 to 7.7 mol per litre, the concentration of nitric acid, in the size reduction etch solution, being in the range 10.4 to 14.2 mol per litre, and the concentration of ethanoic acid, in the size reduction etch solution, being in the range 0.0 to 1.74 mol litre.

According to a fifth aspect, the invention provides a method of fabricating a carrier component, suitable for use in a microprojectile delivery device, comprising the steps: (a) taking a sample of silicon and (b) forming particles from the silicon, step (b) being performed in such a manner that a particulate product comprising at least one microprojectile is formed, and (e) assembling the particulate product with a carrier body in such a manner that the product is retained by the body to form a carrier component.

The silicon may comprise bulk crystalline silicon and/or polycrystalline and/or porous silicon.

The method of fabricating a carrier component may comprise the further step (c) of porosifying said sample of silicon.

Step (c) may be performed before or after step (b).

The method of fabricating a carrier component may comprise the step (d), performed prior to steps (b) and (c), of forming the sample of silicon by depositing a layer of polycrystalline silicon on a substrate.

Advantageously step (b) is performed in such a manner that the or at least one of the microprojectiles has a size in the range 1 nm to 500 μm. More advantageously the or at least one of the microprojectiles has a size in the range 1 nm to 250 μm.

Step (b) may be performed in such a manner that the or at least one of the microprojectiles has a size in the range 10 μm to 100 μm. Step (b) may be performed in such a manner that the or at least one of the microprojectiles has a size in the range 10 μm to 70 μm. Step (b) may be performed in such a manner that the or at least one of the microprojectiles has a size in the range 1 μm to 15 μm.

Preferably step (d) comprises the step of reacting a silicon containing gas in the region of the substrate. More preferably step (d) comprises the step of pyrolysing a silane and/or halogen substituted silane in the region of the substrate. Yet more preferably step (d) comprises the step of pyrolising $SiH_4$ in the region of the substrate.

According to a sixth aspect, the invention provides a method of fabricating a delivery device comprising the steps: (a) taking a sample of silicon, and (b) forming particles from the silicon, step (b) being performed in such a manner that at least one microprojectile is formed, and (f) assembling an activatable gas source and the microprojectile(s) to form a microprojectile delivery device, the gas source and microprojectile(s) being arranged in such manner that, when activated, the gas source causes gas to impart kinetic energy to the microprojectile(s).

The method of fabricating a microprojectile delivery device may comprise the further step (c) of porosifying said sample of silicon.

The silicon may comprise bulk crystalline silicon and/or polycrystalline and/or porous silicon.

Step (b) may be performed before or after step (c).

The method of fabricating a microprojectile delivery device may comprise the step (d), performed prior to steps (b) and (c), of depositing a layer of polycrystalline silicon on a substrate.

Preferably step (d) comprises the step of reacting a silicon containing gas in the region of the substrate. More preferably step (d) comprises the step of pyrolysing a silane and/or halogen substituted silane in the region of the substrate. Yet more preferably step (d) comprises the step of pyrolising $SiH_4$ in the region of the substrate.

Advantageously step (b) is performed in such a manner that the or at least one of the microprojectiles has a size in the range 1 nm to 500 μm. More advantageously the or at least one of the microprojectiles has a size in the range 1 nm to 250 μm.

Step (b) may be performed in such a manner that the or at least one of the microprojectiles has a size in the range 10 μm to 100 μm. Step (b) may be performed in such a manner that the or at least one of the microprojectiles has a size in the range 10 μm to 70 μm. Step (b) may be performed in such a manner that the or at least one of the microprojectiles has a size in the range 1 μm to 15 μm.

According to an seventh aspect the invention provides a method of transfecting at least one cell, the method comprising the steps: (a) taking a microprojectile comprising silicon, (b) combining the particle with a sample of DNA, and (c) implanting the microprojectile in the or at least one of said cells by microprojectile implantation.

Preferably the microprojectile comprises porous and/or polycrystalline silicon.

According to an ninth aspect the invention provides the use of porous and/or polycrystalline silicon, in the preparation of a microprojectile for the delivery of a physiologically active substance to a subject.

Whilst many countries do not, yet, permit the patenting of methods of treatment of the human or animal body by surgery or therapy, there are some (e.g. USA) who do. In order for there to be no doubt about the Paris Convention priority entitlement to such an invention in those countries that do permit it, the invention also comprises the treatment, therapeutic or prophylactic, of a disorder of the human or animal body by microprojectile implantation of at least one microprojectile comprising porous and/or polycrystalline silicon; and allowing the release of an beneficial substance which helps to alleviate or ameliorate the disorder, or to prevent the disorder from occurring.

A "beneficial substance" is something beneficial overall: it could be a toxin, toxic to undesirable cells or to interfere with an undesirable physiological process. For example, anti-cancer substances would be considered "beneficial", even though their aim is to kill cancer cells.

According to an eleventh aspect, the invention provides a use of a particulate product comprising at least one silicon particle for the manufacture of a medicament for the treatment of a patient by microprojectile injection.

Advantageously the or at least one of the silcon particles is a microprojectile.

Advantageously the or at least one of the silicon particles further comprises an active substance.

The active substance may comprise one or more of: a pharmaceutical material, a biological material, a genetic material, a radioactive material, an antibacterial agent, and luminescent agent.

The active substance may comprise one or more of: insulin, lidocaine, anaesthetic, alprostadil, calcitonin, DNA, RNA, peptide, cytokine, hormone, antibody, cytotoxic agent, adjuvant, steroid, and protein.

The active substance may comprise one or more of: GnRH, Goserilin, Leuprordin Acetate, Triptordin, Buserelin, a GnRH agonist, a GnRH superagonist, a GnRH antagonist, a GnRH homologue, a GnRH analogue, and a GnRH mimic.

For the purposes of this specification the term active substance means any substance to be transferred into a target cell or tissue or into a patient.

Advantageously the active substance comprises DNA or RNA.

Advantageously the or at least one of the silicon particles comprises porous silicon having a porosity between 1% and 90%. More advantageously the porous silicon has a porosity between 10% and 80%.

Preferably the or at least one of the silicon particles may have a size in the range 100 nm to 500 $\mu$m. More preferably the or at least one of the silicon particles has a size in the range 100 nm to 250 $\mu$m.

The or at least one of the silicon particles may have a size in the range 10 $\mu$m to 100 $\mu$m. The or at least one of the silicon particles may have a size in the range 10 $\mu$m to 70 $\mu$m. The or at least one of the silicon particles may have a size in the range 1 $\mu$m to 15 $\mu$m.

Advantageously the particulate product comprises at least five substantially single sized silicon particles, each single sized silicon particle having a volume that is substantially identical to the volume of the other single sized particles. More advantageously the particulate product comprises at least ten substantially single sized silicon particles, each single sized silicon particle having a volume that is substantially identical to the volume of the other single sized particles. Yet more advantageously the particulate product comprises at least twenty substantially single sized silicon particles, each single sized silicon particle having a volume that is substantially identical to the volume of the other single sized particles.

Preferably the particulate product comprises a multiplicity of single shaped silicon particles, each single shaped silicon particle having the substantially same shape as the other single shaped silicon particles. More advantageously each single shaped silicon particle has the substantially the same volume as the other single shaped silicon particles. Yet more advantageously each single shaped silicon particle is substantially symmetric.

The total mass of the single shaped silicon particles, from which the particulate product is at least partly formed, may be greater than 10% of the total mass of the particulate product. The total mass of the single shaped silicon particles, from which the particulate product is at least partly formed, may be greater than 50% of the total mass of the particulate product.

The particulate product may comprise a multiplicity of silicon particles and at least some of said silicon particles may be monodispersed.

Advantageously the or at least one of the silicon particles is substantially symmetric. More advantageously the particualte product comprises a multiplicity of substantially symmetric silicon particles, each substantially symmetric silicon particle being substantially symmetric.

The or at least one of the silicon particles may be substantially cubic. The or at least one of the silicon particles may be substantially spherical.

For the purposes of this specification the term "symmetric", when used to describe an object, means that the object comprises at least one plane of symmetry and/or at least one axis of symmetry.

BRIEF DESCRIPTION OF THE DRAWINGS

Embodiments of the invention will now be described by way of example, with reference to the accompanying drawings, in which:

FIG. 1 shows a schematic diagram of a microprojectile delivery device according to the invention;

FIG. 3 shows an SEM image of silicon cubes and spheres produced by a combination of mechanical processing and etching;

FIG. 10 shows a K$\alpha$ energy dispersive x-ray elemental distribution map for porous silicon particles embedded in a gelatine target;

DETAILED DESCRIPTION OF THE INVENTION

Microprojectile Delivery Device

Figure 2A:
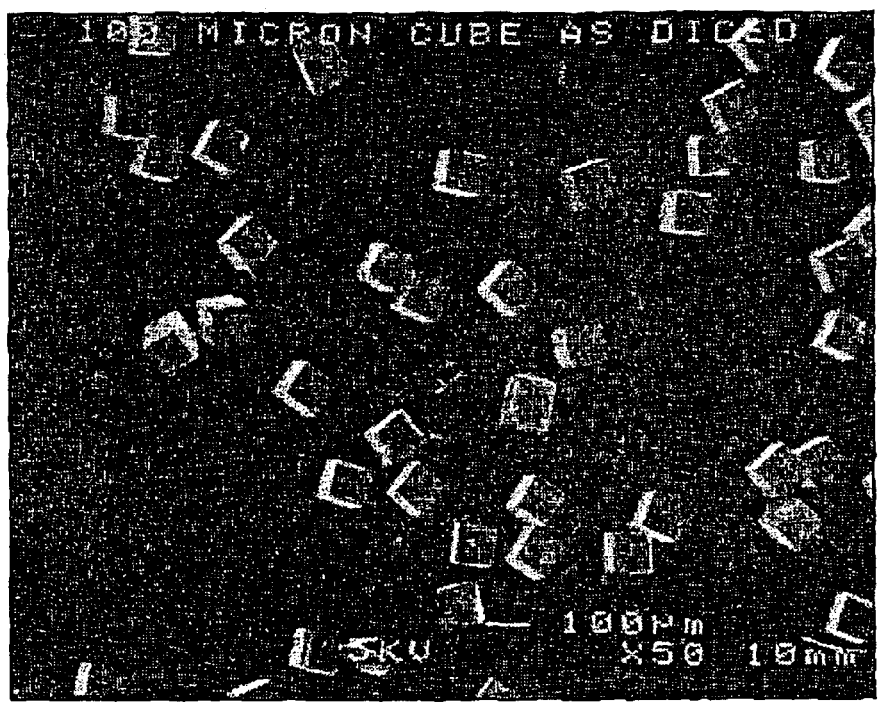
FIG. 2 contains a SEM images of a silicon cubes formed by dicing a silicon wafer.

FIG. 1 shows a schematic diagram of a microprojectile delivery device, generally indicated by 10, according to the invention. The delivery device 10 comprises a carrier component, generally indicated by 12, a gas source 13 and exit system 15. The carrier component 12 comprises a carrier body 16 and a multiplicity of microprojectiles 17. An active substance will typically form part of the microprojectile 17. The active substance may be coated on of the surface of each microprojectile or located, at least partly, in interior of each microprojectile. The fabrication of microprojectiles 17 and the association of an active substance with the microprojectiles 17 is discussed below.

The carrier body 16 is tubular in shape and the microprojectiles 17 are adhered to the interior surface of the carrier body 16. The carrier component 12 is connected, via the valve 13b, to the gas source 13. The gas source 13 comprises a gas cylinder 13a and a gas valve 13b. The gas cylinder 13a, containing a compressed gas, is activated by opening the valve 13b for a short interval. Activation of the gas source 13 in this way causes a pulse of gas to be released. The released gas passes through the carrier component 12 and as it does so some of the microprojectiles 17 are dislodged and entrained in the flow of gas. The microprojectiles 17 pass through the exit system 15 and travel to a target 18. The target 18 may comprise cells or tissue. For example the target 18 may be a human or animal patient. The design of the exit system 15 will determine the manner in which the microprojectiles 17 are delivered to the target 18; for example it may determine the trajectory or the degree of dispersion of the microprojectiles 17.

There are a number of methods by which a particulate product comprising silicon may be fabricated.

Fabrication of a Particulate Product Comprising Silicon Particles

The following processes (numbered 1 to 12) each describe the fabrication of a particulate product comprising at least one silicon particle. Each of these processes may be used to fabricate a particulate product comprising at least one silicon microprojectile.

Process 1

A silicon wafer may be anodised in an HF solution, for example a 50% aqueous or ethanolic solution, to form a layer of porous silicon. The anodisation may be carried out in an electrochemical cell by standard methods such as that described in U.S. Pat. No. 5,348,618. For example a wafer may be exposed to an anodisation current density of between 5 and 500 mAcm$^2$ for between 1 and 50 minutes. In this way a layer of porous silicon having a porosities in the range 1% to 90% may be fabricated. The porous silicon layer may then be detached from the underlying bulk substrate by applying a sufficiently high current density in a relatively dilute electrolyte, for example a current density of greater than 50 mAcm$^{-2}$ for a period of 10 seconds. Alternatively the anodised wafer may be treated ultrasonically to detach the layer of porous silicon and to break up the layer into particles of porous silicon. Exposure to ultrasound in this way may be performed in a solvent, the solvent being chosen to minimise agglomeration of the resulting particles. Some control over particle sizes may be achieved by centrifuging the resulting suspension to separate the different particle sizes. The porous silicon particles may also be sized by allowing the suspension gradually settle as described in Phys. Solid State 36(8) 1294–1297 (1994). Control over silicon particle shape may be attained by size and shape distribution analysis such as laser diffraction analysis, electrozone sensing, hydrozone focussing, and sheath flow technology.

Silicon powders of micron particle size are available commercially. Such commercially available particulate products have silicon particles that have irregular shapes, and that exhibit a wide range of particle sizes. Nanometre size particles can be fabricated from silicon wafers by processes such as ball milling, sputtering, and laser ablation of bulk silicon.

Process 2

A silicon on insulator (SOI) wafer may be photolithographically etched by standard wet etch or dry etch techniques such as those described in PCT/GB99/02381. The etch may be performed in such a manner that an array of silicon microprojectiles are formed on the oxide substrate. The microprojectiles may have dimensions in the range 10 to 250 $\mu$m. The microprojectiles can be detached from the oxide substrate by standard HF soak. The microprojectiles can then filtered off, washed and dried prior to porosification. In this way a particulate product comprising porous silicon particles of monodispersed size and shape may be obtained.

Alternatively, and more specifically, a 20 to 30 $\Omega$cm p type (100) silicon wafer with a 10 micron thick p++ top layer is coated on both sides with 100 nm of silicon oxide. The silica layer on the back of the wafer is then patterned with a membrane photomask and reactive ion etched to define the wafer area to be thinned. A supported 10 micron thick membrane is then realised by wet etching through from the back of the wafer to the p++/p− interface. For a 475 micron thick wafer and KOH at 80C. this takes 10 to 15 hours. Thick photoresist is then deposited in the back etched cavity as a support for the membrane and as a substrate from which the silicon particles may be removed. Positive photoresist is spun on the front face of the wafer and pattered with a photomask containing thousands of 10×10 micron spaced squares. The silica and p++ membrane are then reactive ion etched. The thick photoresist/diced silicon membrane is then removed from the wafer and placed in a centrifuge tube. The silicon cubes can then be released by dissolving the photoresist in acetone, and collected by centrifugation.

Porosification of the above silicon particles may be achieved by standard stain etching as described in J Applied Physics 78(6) p4273–4275 (1995), or light-assisted stain etching as described in Physical Chemistry Chemical Physics 2(2):277–281, 2000. The lithographically based approach allows the fabrication of silicon particles having a well defined shape and narrow size distribution.

Process 3

Figure 2B:
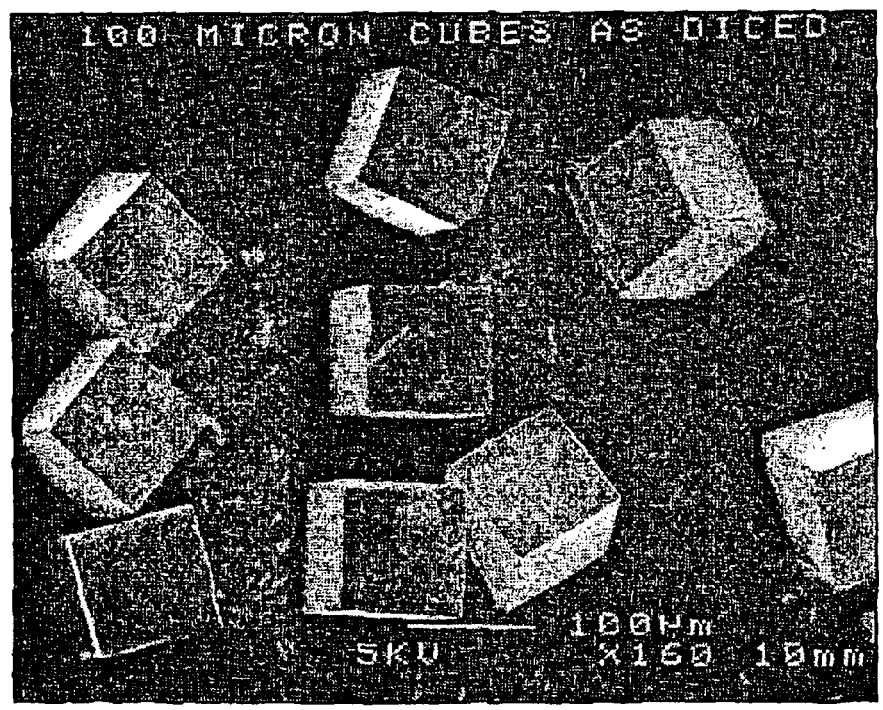
Figure 2C:
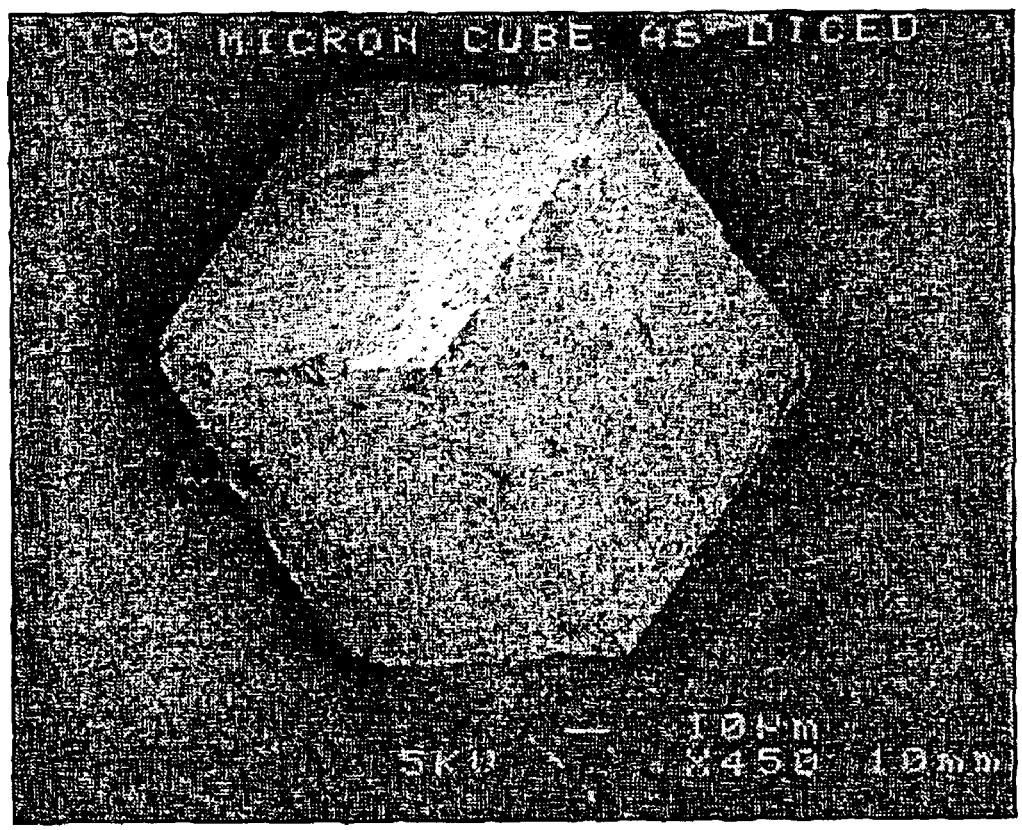

A multiplicity of silicon cubes may be fabricated by dicing a silicon wafer, using MicroAce 3 automated dicing equipment incorporating a 75 micron wide blade impregnated with 4 to 6 micron diamond powder. By appropriately programming of the MicroAce, cubes having substantially the same size as each other are formed, as shown in FIGS. 2a to 2c. The cube dimensions are approximately equal to the thickness of the wafer from which they were formed. Cubes having dimensions in the range 100 microns to 2 mm may be fabricated by this method. The cubes shown in FIGS. 2a and 2b are substantially monodispersed, having uniform dimensions and shapes. As can be seen the cube shown in FIG. 2c is substantially symmetric, though there is a small amount of saw, damage in the form of small chips and irregularities on four of the six faces.

Process 4

Further mechanical processing may then performed on the cubes, formed by process 3, to convert them into substantially spherical beads. The cubes were introduced to a spherical drum, lined with an abrasive paper. The drum comprises an array of directed nozzles, located at the centre of the drum, through which a stream of compressed gas flows. The compressed gas causes the silicon particles to be blown around a circular trajectory within the drum. Experiments were performed, on 2 mm wide cubes, at 20 to 40 psi for 5 to 60 minutes using a 200 micron filter to remove unwanted silicon dust. Mechanical processing in this way yielded substantially spherical silicon beads having a diameters approximately in the range 1.6 mm to 1.2 mm. The method used to fabricate these particles is similar to that disclosed in "The Review of Scientific Instruments Vol 36(7) p957 to 958 (1965).

Process 5

The silicon cubes, fabricated by process 3, may also be converted to silicon spheres by particle milling. This involves tumbling the silicon particles in an abrasive medium. Suitable particulate milling media include industrial diamond powder, ceramic micro particles, and stainless steel or zirconia balls.

Process 6

Alternatively the cubes, fabricated by process 3, may be converted to silicon spheres by grinding the silicon particles between two rotating plates of sufficiently hard material such as tungsten carbide or preferably plates that have been covered by a thin film of hard abrasive. For example, monodspered silicon spheres may be fabricated, from cubes generated by process 3, by polishing between two flat glass plates covered by 600 grit wet and dry paper. Silicon cubes are first placed onto the centre of the lower plate and then covered in a thin layer of oil, such as Hyprez fluid. The second plate is then placed on top of the cubes and moved in a circular motion. Once the edges of the cubes have been removed, so that the the silicon particles act as bearing for the two plates, a mass of several kg may be applied to the upper plate. Grinding between the two glass plates may be for a period ranging from a few minutes to a several hours.

Figure 6A:
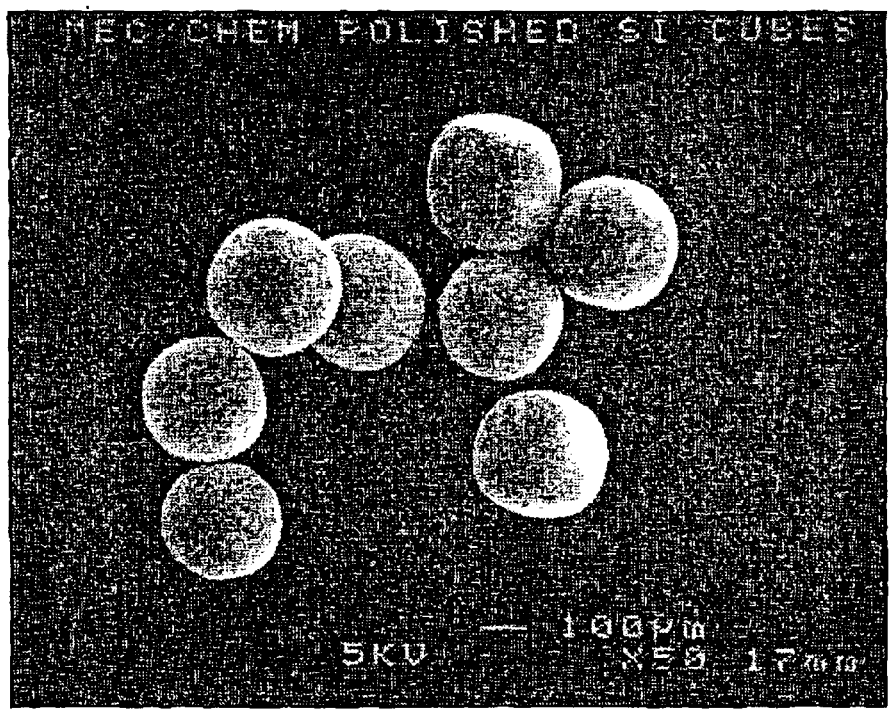
FIG. 6 shows SEM images of bulk crystalline and porous silicon spheres.
Figure 6B:
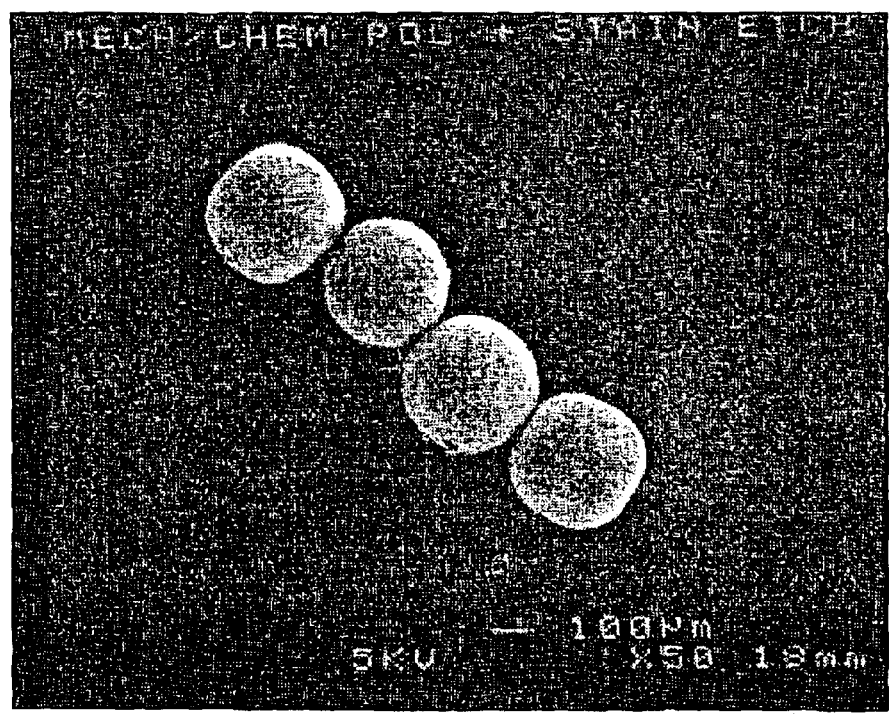
Figure 6C:
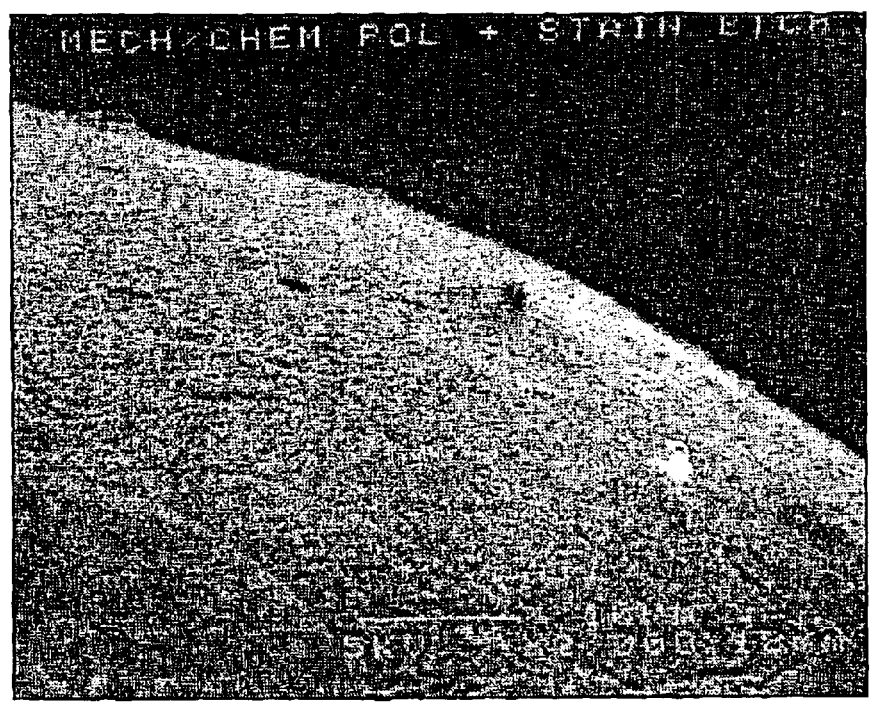

FIG. 6($a$) shows a multiplicity of silicon spheres that have been fabricated by the process 6 method.

Process 7

Silicon particles fabricated by one or more of processes 3 to 6 may further be subjected to a size reduction etch that reduces the size of the particles and also reduces surface damage resulting from mechanical processing. The size reduction etch solution may be formed by combining 5 volumes of 70% aqueous nitric acid, 1 volume a 40% aqueous hydrofluoric acid, and 1 volume substantially pure ethanoic acid; this solution will be referred to as "5:1:1 etch solution".

Silicon particles, fabricated by one or more of processes 3 to 6, were etched in the presence of silicon discs, each disc having a diameter of 1 cm, the mass of silicon discs required was 0.8 g per 35 ml of the 5:1:1 etch solution. FIG. 3 shows four silicon cubes and six silicon spheres of varying sizes. The cubes shown in FIG. 3 were obtained by exposing cubes fabricated by process 3 to the 5:1:1 solution for periods of between 5 and 60 minutes minutes, the length of each side varies from 2 mm (for the largest cube) to 380 microns (for the smallest cube). The spheres shown in FIG. 3 were obtained by exposing spheres fabricated by process 4 to the 5:1:1 etch solution for periods between 5 and 30 minutes, the sphere diameters vary from 1.1 mm (for the largest sphere) to 350 microns (for the smallest sphere).

Process 8

Particulate products, fabricated by one or more of processes 3 to 7, or by the photolithographic technique forming part of process 2, may be porosified by stain etching the silicon particles.

Figure 4:
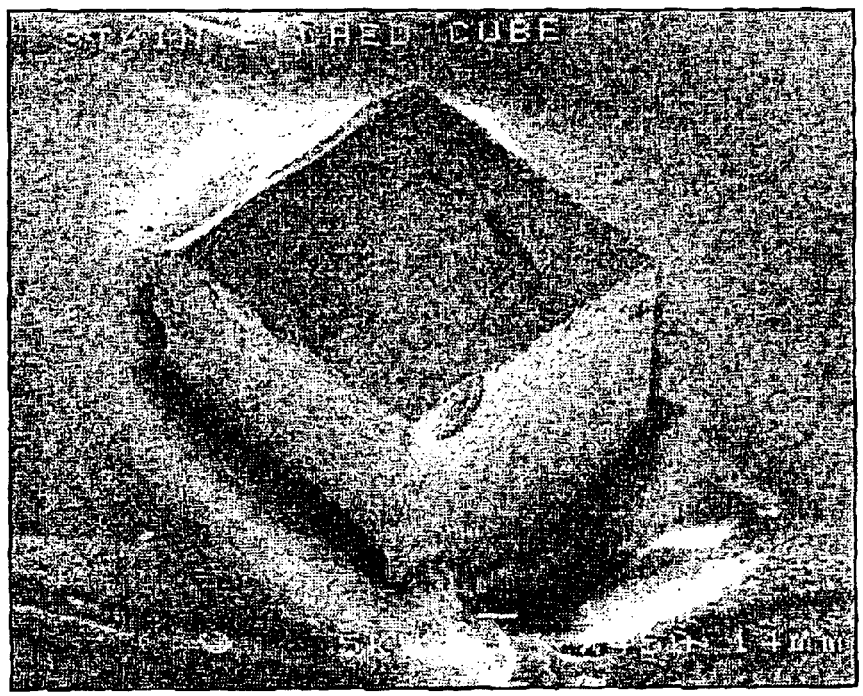
FIG. 4 shows a high magnification SEM image of silicon cube that has been porosified by stain etching.
Figure 5:
FIG. 5 shows an SEM image of a section of a porous silicon cube.

A stain etch solution comprising hydrofluoric acid and nitric acid was employed. The stain etch solution was formed by combining 100 volumes of 40% aqueous hydrofluoric acid solution with 1 volume of 70% aqueous nitric acid solution; this stain etch solution will be referred to as the "100:1 solution". The 100:1 solution may be applied to the particulate product for a period of five minutes to yield silicon particles having a 3.9 micron, 47% porosity, layer of porous silicon. FIG. 4 shows an SEM image of a cube, having sides of length 100 microns, fabricated by process 3, and porosified by treatment with the 100:1 etch solution for a period of 10 mintutes. FIG. 5 shows an SEM image of a section of a silicon cube, having sides of length 100 microns, fabricated by process 3, and porosified by treatment with the 100:1 etch solution for a period of 10 minutes. The section shown in FIG. 5 is a corner of the cube, and the image shows a layer of porous silicon that has been formed at the periphery of the cube.

The FIG. 4 image may be compared with that of FIG. 2$c$. The FIG. 2$c$ image was taken at the same maginifcation as the FIG. 4 image, and shows a cube having the same dimensions as the FIG. 4 cube. However, the FIG. 2$c$ cube has not been porosified. A comparison of the two images shows that porosification using the 100:1 etch solution need not result in any substantial change in size or shape. This is markedly illustrated by the continued presence of saw damage in the FIG. 4 cube.

FIGS. 2$a$ and 2$b$ show monodispersed un-porosified silicon particles, and FIGS. 2$c$ and 4 show that porosification causes negligible change to size and shape. Therefore the results shown in FIGS. 2 and 4 show that it is possible to fabricate a monodispersed particulate product comprising porous silicon particles having a largest dimension less than 500 microns.

The use of a stain etch may not only cause porosification of the sample of silicon to which it is applied, but it may also dissolve at least some of the porous silicon that is so formed. This dissolution may limit the thickness of porous silicon that can be achieved by stain etching.

FIG. 6($b$) shows four porous silicon spheres that have been fabricated by the process 6 method followed by stain etching according to the process 8 method. FIG. 6($b$) shows a higher magnification image of one of the porous silicon spheres shown in FIG. 6($b$).

Process 9

Ion bombardment of the particulate product may, at least partially, solve the problem of dissolution associated with stain etching. For example Si, F, Cl, H, He, and Ar ions, may be used to bombard the silicon of the particualte product. Alternatively neutrons or electrons may also be used. Such bombardment introduces point defects or extended defects in the sample of silicon. The presence of the defects allows the use of a less chemically aggressive stain etch solutions that, for a given rate of porosification, cause less dissolution. The use of particle bombardment followed by porosification in this way is described in Jpn J Appi Phys Vol 31 (5A) p L560–L563 (1992) and in Semiconductors 30 (6) p 580–584 (1996). The use of lighter elements may be of particular value, for example 2 MeV H+ has a projected range of 50 microns, potentially opening the way for the use of less aggressive stain etch solutions over a range of several tens of microns.

Process 10

Silicon particles may also be fabricated using polycrystalline silicon, by the process steps illustrated in FIG. 7. A layer of phosphosilicate glass 21 (PSG) may be deposited on a silicon substrate 22. The deposition may be performed using atmospheric pressure CVD by reacting pure silane and phosphine with oxygen in a nitrogen stream. The PSG 21 may then be patterned by conventional techniques to form an array of base structures 23. A layer of polycrystalline silicon (not shown in FIG. 7) can then deposited by pyrolysis of silane using low pressure CVD. The polycrystalline silicon layer is then patterned, by standard etching techniques, in such a manner that each base structure is enveloped in an island layer of polycrystalline silicon 24, and that the island layer is also bonded to the silicon substrate adjacent to the base structure. Heating the polysilicon layer to temperatures between 950 and 1100C for 10 to 30 minutes causes the polysilicon layer to deform (as shown in FIG. 7*d*) as a result of the release of $P_2O_5$ from the PSG. By selecting the correct form of patterning and conditions the detached silicon particles comprising shell like structures may be used for microprojectile implantation.
Process 11

Silicon has a low density relative to some materials (such as gold and tungsten) currently used in the fabrication of microprojectiles for intercellular delivery. The ability of a microprojectile to penetrate a cell wall or tissue depends to some extent on its momentum and hence on its mass. It may therefore be necessary, for some applications, to increase, the density of a silicon microprojectile. This may be done by introducing an element or compound to the microprojectile that has a density greater than that of silicon. There are a number of ways in which such elements may be introduced. A review of porous silicon impregnation is presented in the book "Properties of Porous Silicon", Chapter 1.9, p 66 to 76, Published by INSPEC (ISBN 085296 932 5). A further group of methods of impregnation is described in PCT/GB99/01185. For example silver nitrate powder may be placed onto the surface of a sample of porous silicon. The silver nitrate and porous silicon may then be heated in an argon atmosphere until the nitrate is observed to melt and decompose. The molten nitrate enters the pores where it decomposes thereby depositing silver within the porous silicon.
Process 12

Figure 8:
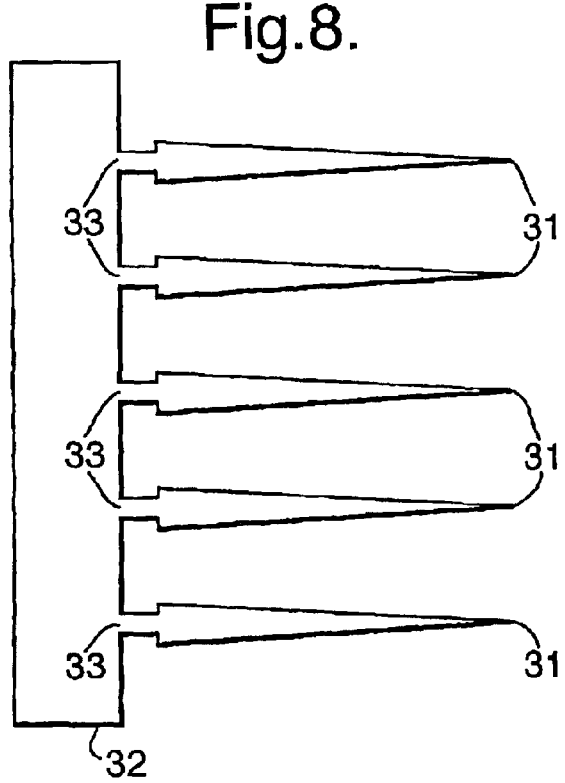
FIG. 8 shows a schematic diagram of a plurality of microprojectiles comprising an array of microneedles.
Figure 7A:
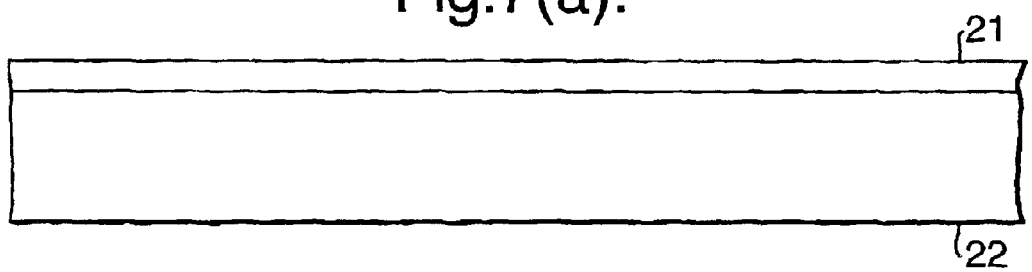
FIG. 7 illustrates a method of fabricating a particulate product according to the invention.
Figure 7B:
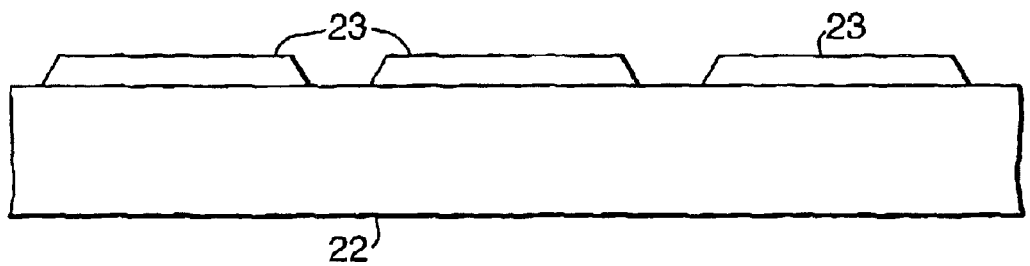
Figure 7C:
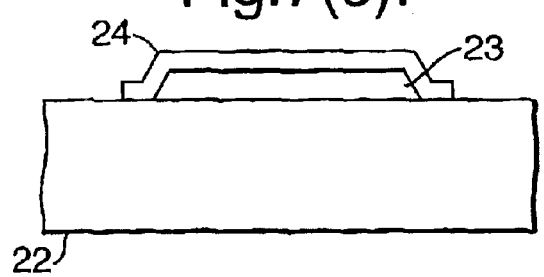
Figure 7D:
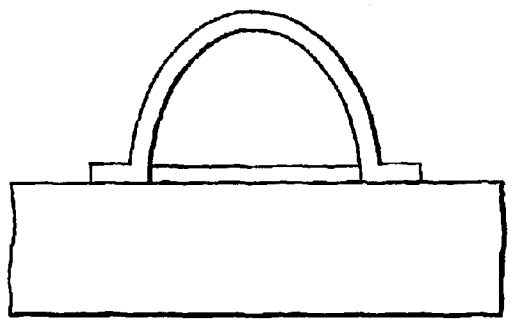

As mentioned in the last paragraph the problem associated with silicon's low density may be overcome by impregnation of the microprojectile with an element or compound. A further way in which this problem can be overcome is to form the microprojectiles from an array of microneedles as shown in FIG. 8. Such an array 31 may be formed by standard wet etching techniques such as those described in IEEE Transactions in Biomedical Engineering Vol 38, No 8, August 1991, p 758 to 768.

Specifically, two sets of deep (200 micron) orthogonal cuts are made into a 380 micron thick wafer. The wafer is rotated by 90 degrees between the first set of n cuts in one direction, and the second set of m cuts in the orthoganal direction. This sawing does not cut through the wafer at any point but creates an array of n×m square columns having an aspect ratio determined by the spacing of the cuts. For a 75 micron wide blade and a pitch of 175 microns one creates 100 micron wide square columns. The subsequent etching processes to define dart-like shapes then have 3 steps. The first chemical etch is to remove saw damage, isotropically reduce the width of the columns and round the edges at the base of the columns. It utilizes an HF: HNO3 etch (eg 5% to 95%) that is conducted with vigorous agitation. The second chemical etch is performed under static conditions that promote preferential attack of the top of the columns to create pointed tips and a tapered shaft. The third etch step is to create a mechanical weakness at the base of the columns which facilitates their detachment from the underlying silicon membrane. This can be achieved by the use of dry etch conditions that undercut the columns.

FIG. 8 shows a schematic diagram of an array of silicon microneedles 31 that is integral with a substrate 32. The substrate 32 may form a particle carrier or part of a particle carrier suitable for loading in a microprojectile delivery device similar to that shown in FIG. 1. The substrate 32 and gas source may be arranged such that the gas impacts with the side of the substrate 32 opposite to that on which the microneedles 31 are formed. This differs from the arrangement shown in FIG. 1 in which the surface in which the microprojectiles are arranged is roughly parallel to the direction of gas flow. Impact of the gas with the substrate 32 would then cause the microneedles 31 to break away from the substrate and to become incident upon the target. The process may be facilitated by forming a narrow neck portion 33 adjacent to the substrate.

The narrow neck portions at the base of the needles may be formed by standard deep dry etching techniques in combination with an etch stop (eg silicon oxide).
Incorporation of an Active Substance into a Particulate Product There are a number of methods by which the particulate product may be made to comprise the active substance. This section describes the fabrication of silicon particles comprising an active substance. The methods of fabrication described in this section may be suitable for fabricating silicon microprojectiles comprising an active substance.

The method selected will depend on a number of criteria including: (a) the nature of the active substance to be loaded in the silicon particle, (b) the dose or loading required, (c) the pharmacokinetic release profile required for optimal delivery of the active substance in question, (d) whether a derivatised form of silicon is preferred, (e) the hydrophilicity/hydrophobicity profile of the active substance to be loaded, and (f) whether an active substance release mechanism is required over and above the rate of dissolution of the silicon particle in order to effect drug release.

The following methods may be applied to load porous silicon microprojectile implants:
Liquid or Solution Phase Loading The active substance may be converted to a liquid form by dissolution or suspension in an aqueous, organic or amphypathic phase. Alternatively the active substance may be a liquid at room temperature or it may be made liquid by exposure to an appropriate temperature and/or pressure. The active substance, in liquid form, can then be taken up by porous silicon particles by bringing the particles into direct contact with the active substance. Porous silicon exhibits substantial capilliarity and as a consequence, the liquid phase active substance may be drawn into the porous silicon material by capillary action. If a solution or suspension of the active substance has been used, the microprojectile may then be dried by conventional freeze drying or other routinely practiced drying techniques. The steps of liquid/solution loading followed by drying may be repeated a number of times to increase the amount of active substance in each porous silicon particle.

Alternatively the silicon particles comprising porous silicon and an active substance may be fabricated by forming a disc of porous silicon in the manner described in process 1. Such a disc may then be used as a filter for a suspension or solution of an active substance in a suitable liquid carrier or solution. As the solution or suspension passes through the porous silicon filter, the active substance may be deposited onto the porous silicon. The porous silicon disc, on which the active substance has been deposited, may then be converted to a particulate product, comprising silicon particles, by the method described in Process 1.

Solid Phase Loading

Finely divided porous silicon may be combined with a finely divided form of an active substance in the solid phase by such techniques as spray coating techniques and pressure based techniques. The finely divided silicon/active substance is moulded to form silicon particles of the required mass, shape and dimensions. The use of highly porous silicon comprising quantum wires is of particular value for this technique, the finely divided silicon being formed by crushing the porous silicon.

Derivatisation and Sequestration

Porous silicon may be derivatised by techniques similar to those described in J M Buriak, J Chem Soc, Chem Commun p 1051, 1999, in such a manner that a biomolecule, having a high affinity for a particular active substance, is bonded to the surface of the porous silicon. Biomolecules that might be suitable for this application include antibodies, enzymes, hormones, receptors, proteins, and peptides. The derivatised porous silicon may then be combined with the active substance by methods described in this section, the active substance forming a bond to the porous silicon by means of the biomolecule. The porous silicon may then be converted to a particulate product by the method described in Process 1.

Electronic Precipitation

A further method by Which porous silicon may be combined with an active substance is by electronic precipitation. A sample of porous silicon may be placed in a solution containing cations or anions of the active substance. The porous silicon may then be biased in such a manner that the cations or anions of the active substance are attracted to the porous silicon. The porous silicon may then be converted to a particulate product by the method described in Process 1.

The active substance (for example DNA) may be dissolved or suspended in a suitable solvent, the microprojectiles may then be incubated in the resulting solution for a period of time. The active substance may then be deposited on the surface of the microprojectiles. If the microprojectiles comprise porous silicon, then a solution of the active substance may be introduced into the pores of the porous silicon by capillary action. Similarly if the microprojectiles have a cavity then the solution may also be introduced into the cavity by capillary action. If the active substance is a solid but has a sufficiently high vapour pressure at 20C. then it may be sublimed onto the surface of the microprojectiles. If a solution or suspension of the active substance can be formed then the substance may be applied by successive immersion in the solution/suspension followed by freeze drying.

Microprojectile Injection of Bulk Crystalline and Porous Silicon Particles into Tissue Simulant.

Two types of particulate product were tested. The first type of product comprises porous silicon microprojectiles produced by process 1, and the second particulate product comprises cubic silicon microprojectiles fabricated by process 3. The density of the porous silicon particles was approximately 1.1 g cm$^{-3}$. The first and second particulate products were accelerated, from an initial stationary state, towards a target tissue simulant.

The target tissue simulant comprised gelatine, and was fabricated following a modified NATO standard procedure AC/225114 (1980). Dry gelatin powder was mixed with water at a concentration of 20% by weight. The mixture is gelatinous and opaque. Then, without stirring, it was heated to 50C. to yield a clear, easy flowing liquid. Any foam or bubbles on the surface were skimmed off, prior to pouring the liquid into suitable plastic moulds. The mixture was gradually cooled while in the mould to a temperature of 20C. and then stored at 10C. for two days prior to use.

The two types of particulate product were accelerated using a 0.5 inch diameter Browning slave barrel device and 3N Vihtavouri propellant. During acceleration along the barrel, the particulate product was housed in a cylindrical cavity with a nylon sabot. This housing was selectively stopped from reaching the gelatine block by a stainless steel "stripper plate" containing a hole that allows the passage of the particulate product, but not the sabot. The speed of sabot and its contents, upon exiting the barrel was 700 metres per second. The speed was measured using a Terma Electronik AS Doppler Instrument (DR5000 Model), triggered by the muzzle flash.

Figure 12:
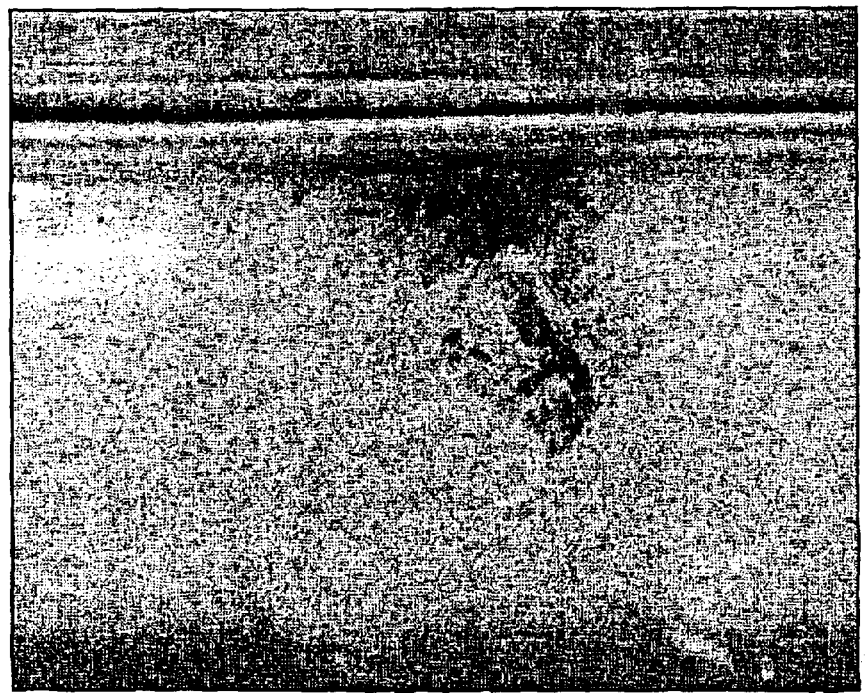
FIG. 12 shows optical microsope image of a silicon particle trajectory in gelatine block in cross-section.

FIG. 12 shows a typical cross sectional image, from an optical microscope, showing a cavity formed in the gelatine as a result of the microprojectile injection of the silicon microprojectiles.

Figure 9A:
FIG. 9(a) shows a backscattered electron micrograph of porous silicon particles embedded in a gelatine target.
Figure 9B:
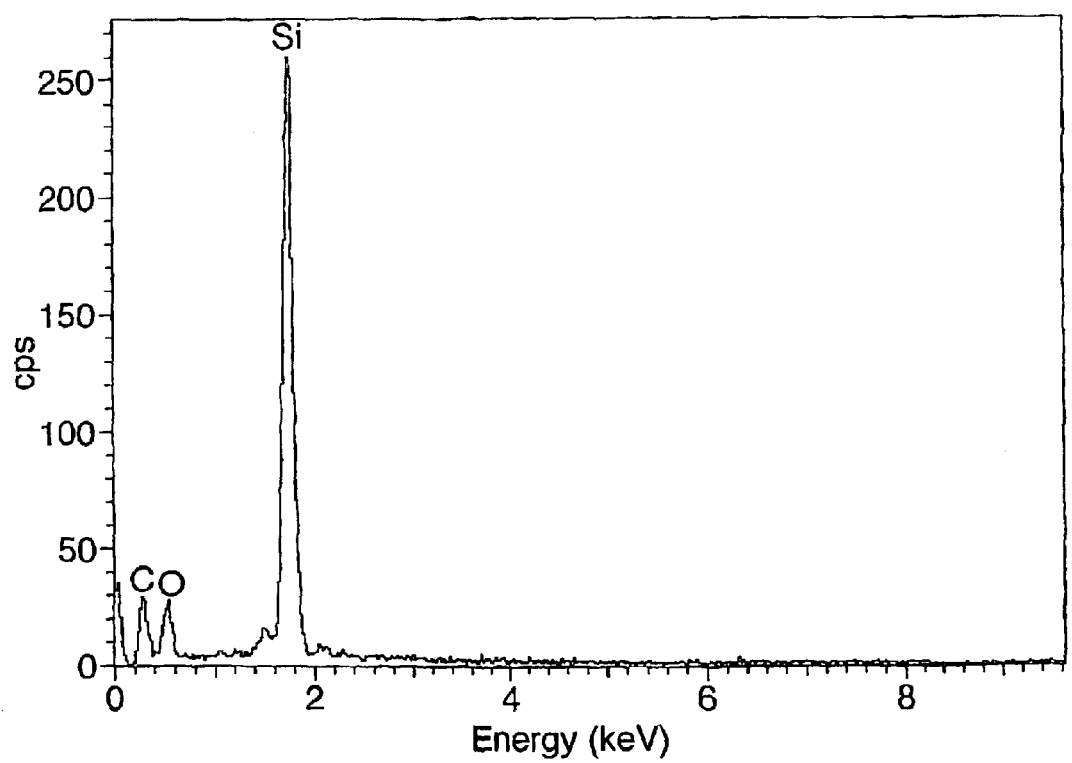
FIG. 9(b) shows an EDX elemental distribution corresponding to the FIG. 9(a) image for porous silicon particles embedded in gelatine.
Figure 11:
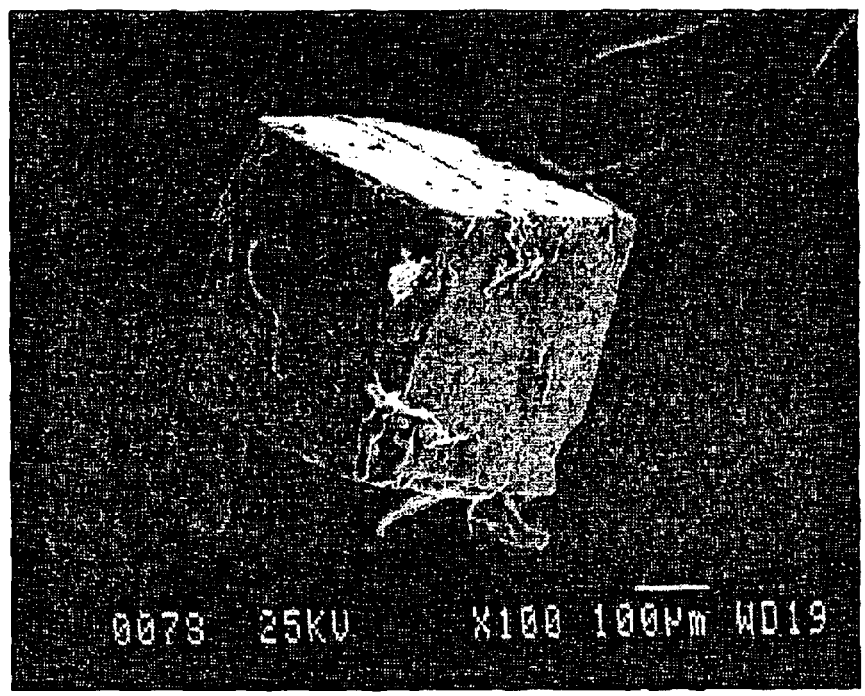
FIG. 11 shows an SEM image of bulk crystalline silicon cube that has been recovered from a gelatine target.

FIG. 9(b) shows an image taken from the region of the cavity close to the point at which the microprojectiles enter the gelatine. The FIG. 9(b) image is an electron micrograph of the gelatine in this region, and it shows porous silicon particles (pale grey) surrounded by the cavity (dark grey). The corresponding EDX elemental distribution is shown in FIG. 9(b). FIG. 10 shows a Kα energy dispersive x-ray elemental distribution map for porous silicon particles embedded in the same region. FIGS. 9 and 10 show that wholly porous silicon microprojectiles have acquired sufficient momentum to penetrate the tissue simulant. FIG. 11 shows an SEM image of a cube that has been retrieved from the tissue simulant. The cube had penetrated several mm into the gelatine. The image shows that the cube has been substantially undamaged by the acceleration and deceleration caused by the microprojectile injection.

What is claimed is:

1. A particulate product comprising monodispersed porous silicon particles, at least one of the porous silicon particles comprising porous silicon obtainable from a sample of silicon by one or more of: stain etching, anodization, and electrochemical etching.

2. A particulate product according to claim 1 wherein at least one of the silicon particles comprises a cavity that is bounded, at least partly, by the silicon.

3. A particulate product according to claim 1 wherein each of the monodispersed silicon particles has a dimension between 100 nm and 500 microns.

4. A particulate product according to claim 1 wherein each of the monodispersed silicon particles has a largest dimension less than 500 microns.

5. A particulate product according to claim 1 wherein at least one of the silicon particles is a microprojectile.

6. A particulate product according to claim 1 wherein each of the monodispersed silicon particles is a microprojectile and at least one of the microprojectiles comprises a high density material having a density greater than that of bulk crystalline silicon.

7. A particulate product according to claim 6 wherein the high density material is selected from one or more of: gold, tungsten, platinum, iron, nickel, molybdenum, silver, palladium, erbium, iridium, rhenium, and cobalt.

8. A particulate product according to claim 1 or 4 wherein at each of the monodispersed silicon particles is symmetric.

9. A particulate product according to claim 8 wherein at least one of the symmetric silicon particles is spherical.

10. A particulate product according to claim 8 wherein at least one of the symmetric silicon particles is cubic.

* * * * *